(12) United States Patent
Gehring et al.

(10) Patent No.: US 6,333,500 B2
(45) Date of Patent: Dec. 25, 2001

(54) METHOD OF INSPECTING A SUBSTRATE FURNISHED WITH A PHOSPHOR LAYER

(75) Inventors: Frederik C. Gehring; Lambertus J. J. Van Rijsewijk; Pieter Scholten; Petrus J. Uitterhoeve, all of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/172,434

(22) Filed: Oct. 14, 1998

(30) Foreign Application Priority Data

Oct. 15, 1997 (EP) .................................................. 97203224

(51) Int. Cl.⁷ ........................................................ G01J 5/02
(52) U.S. Cl. ........................ 250/341.1; 356/632; 356/51
(58) Field of Search ............................ 250/341.1, 341.4, 250/339.06, 339.09, 339.12; 427/8, 9, 10; 348/189, 190; 252/301.6 P; 313/480, 486; 356/51, 382, 632

(56) References Cited

U.S. PATENT DOCUMENTS

| | | | |
|---|---|---|---|
| 3,764,555 | * | 10/1973 | Vincent et al. ................. 252/301.6 P |
| 3,773,420 | * | 11/1973 | Conroy ................................... 356/51 |
| 4,243,882 | | 1/1981 | Yasujima et al. ...................... 250/339 |
| 4,680,503 | * | 7/1987 | Spierings et al. ...................... 313/480 |
| 5,619,330 | * | 4/1997 | Ehemann, Jr. et al. ............. 356/382 |
| 5,644,193 | * | 7/1997 | Matsuda et al. ....................... 313/486 |

FOREIGN PATENT DOCUMENTS 08162023A    6/1996   (JP) .

* cited by examiner

Primary Examiner—Constantine Hannaher
Assistant Examiner—Shun Lee
(74) Attorney, Agent, or Firm—Norman N. Spain

(57) ABSTRACT

A property of a layer of a phosphor screen on a substrate is determined by sending a beam of infrared radiation through the substrate and the layer and measuring, after the passage, the intensity of the beam. The radiation can be measured by a CCD camera.

8 Claims, 2 Drawing Sheets

METHOD OF INSPECTING A SUBSTRATE FURNISHED WITH A PHOSPHOR LAYER

BACKGROUND OF THE INVENTION

The invention relates to a method of determining a property of a layer of a phosphor screen on a substrate. Said layer may be applied, for example, to the inner surface of a display window of a display device, for example the inner surface of a display window of a cathode ray tube, or to a lamp.

Cathode ray tubes are used, inter alia, in television receivers and computer monitors. Lamps are used in lighting devices.

Display devices, such as cathode ray tubes and plasma display apparatuses, comprise a phosphor screen on an inner surface of a display window. A phosphor screen comprises a number of layers, for example three phosphor layers (red, green and blue), a so-called black matrix layer and, sometimes, color filter layers. The quality of the image displayed by the display device is determined to a substantial degree by the properties of these layers. A method of determining a number of properties of phosphor layers in a cathode ray tube is disclosed, for example, in the English-language abstract of Japanese patent application 08-162023. The position of the phosphor layers is determined by means of optical measurements.

Phosphor layers are also applied to the inner surface of lamps. The quality of the lamps depends on the quality of the applied phosphor layer.

However, a number of properties and, in particular, the thickness of a layer cannot be measured by means of the known method. Hitherto, the thickness is customarily measured by making an incision in a phosphor layer whereafter the thickness is measured. However, this measuring method is destructive, which leads to higher costs and which also means that it is impossible to test a product which is to be sold.

It is an object of the invention to provide a method which enables properties of a layer of a phosphor screen on a substrate, for example the inner surface of a display window of a display device or a lamp, to be determined in a non-destructive manner.

SUMMARY OF THE INVENTION

To achieve this, the method in accordance with the invention is characterized in that the substrate and the layer are exposed to infrared radiation and, after passage through the layer and the substrate, the intensity of the beam is measured in a number of spots.

The invention is based on the recognition that the infrared light transmission of a layer of a phosphor screen is governed by the thickness and porosity of the layer, not, or only to a small degree, by other properties of the substrate and/or the phosphor layer. Other radiation (visible light or UV radiation) is largely absorbed by the material of the substrate (mostly a type of glass) or the material of the layer. Phosphor layers as well as color filter layers and black matrix layers exhibit a high degree of absorption in the visible-light spectrum. As a result, the transmission of visible light or UV radiation is much lower and subject to all kinds of disturbing variations. However, by using infrared light it becomes possible to measure the thickness of the layer (and/or other properties, as will be described hereinbelow) in a simple and non-destructive manner.

The method in accordance with the invention can particularly advantageously be used to determine the layer thickness of the phosphor layer, in which operation, preferably, also the porosity of the phosphor layer is determined.

Preferably, a substantially parallel beam of infra-red radiation is sent through the substrate and the phosphor layer.

The use of a substantially parallel beam enables the thickness of the phosphor layer to be determined more accurately.

The invention also relates to a device for determining a property of a layer of a phosphor screen on a substrate.

The device in accordance with the invention is characterized in that the device comprises a means for holding the substrate, an infrared source for emitting infrared radiation and a recording means for recording or measuring infrared radiation emitted by the source and passed by the substrate and the phosphor layer. Said recording means may be, for example, an infrared camera.

These and other aspects of the invention will be apparent from and elucidated with reference to the embodiments described hereinafter.

DESCRIPTION OF THE PREFERRED EMBODIMENT

Figure 1:
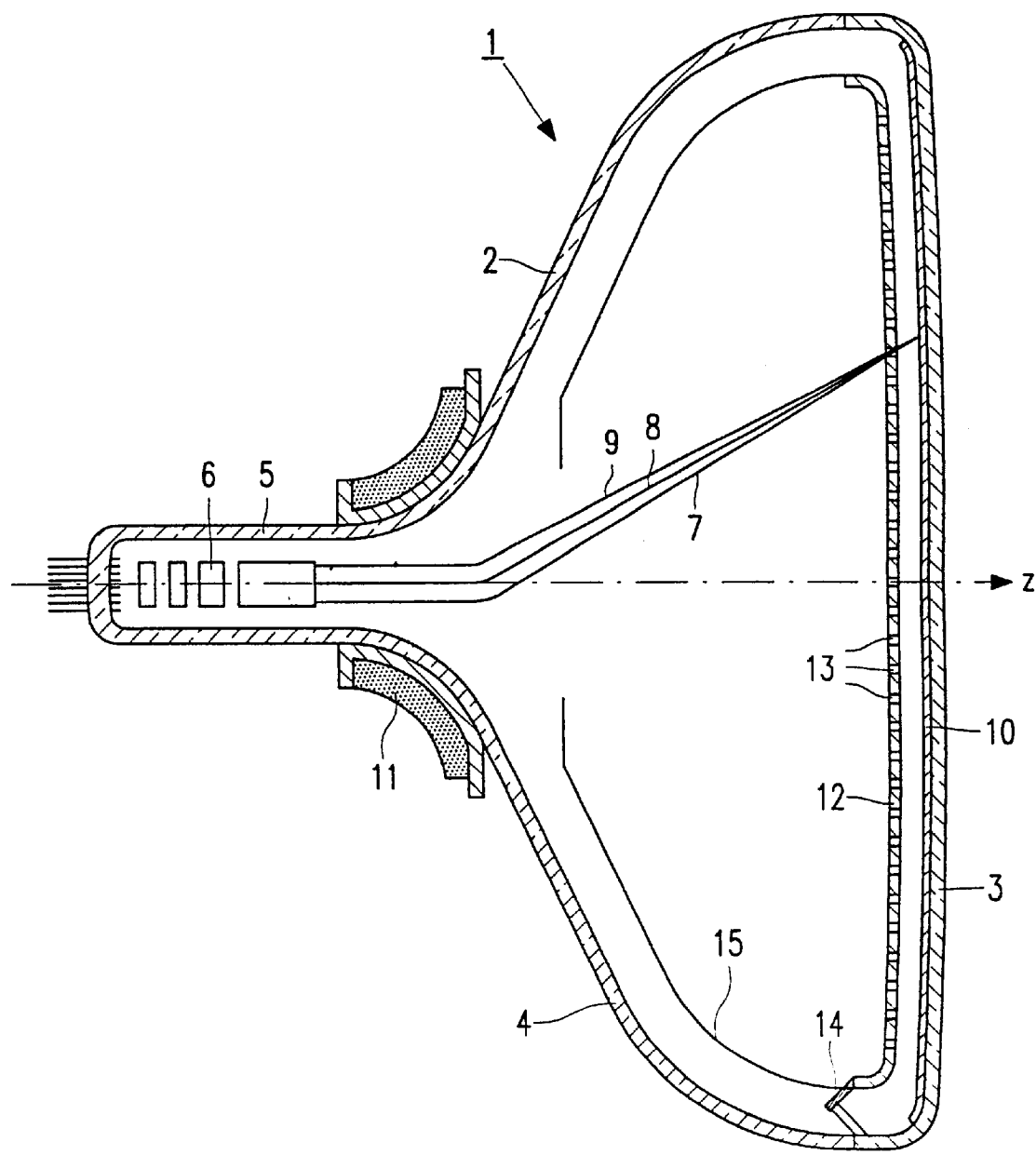
FIG. 1 shows a sectional view of a display device.

The Figures are not drawn to scale. In the Figures, like reference numerals generally refer to like parts.

A color display device 1 comprises an evacuated envelope 2 with a display window 3, a cone portion 4 and a neck 5. Said neck 5 accommodates an electron gun 6 for generating three electron beams 7, 8 and 9. A display screen 10 is situated on the inner surface of the display window. Said display screen 10 comprises a phosphor pattern of phosphor elements luminescing in red, green and blue. On their way to the display screen, the electron beams 7, 8 and 9 are deflected across the display screen 10 by means of a deflection unit 11 and pass through a color selection electrode 12 which is arranged in front of the display window 3 and which comprises a thin plate having apertures 13. The color selection electrode is suspended in the display window by means of suspension means 14. The cathode ray tube may further comprise a magnetic shielding case 15. The three electron beams pass through the apertures of the shadow mask and each electron beam impinges on phosphor elements of only one color.

Figure 2:
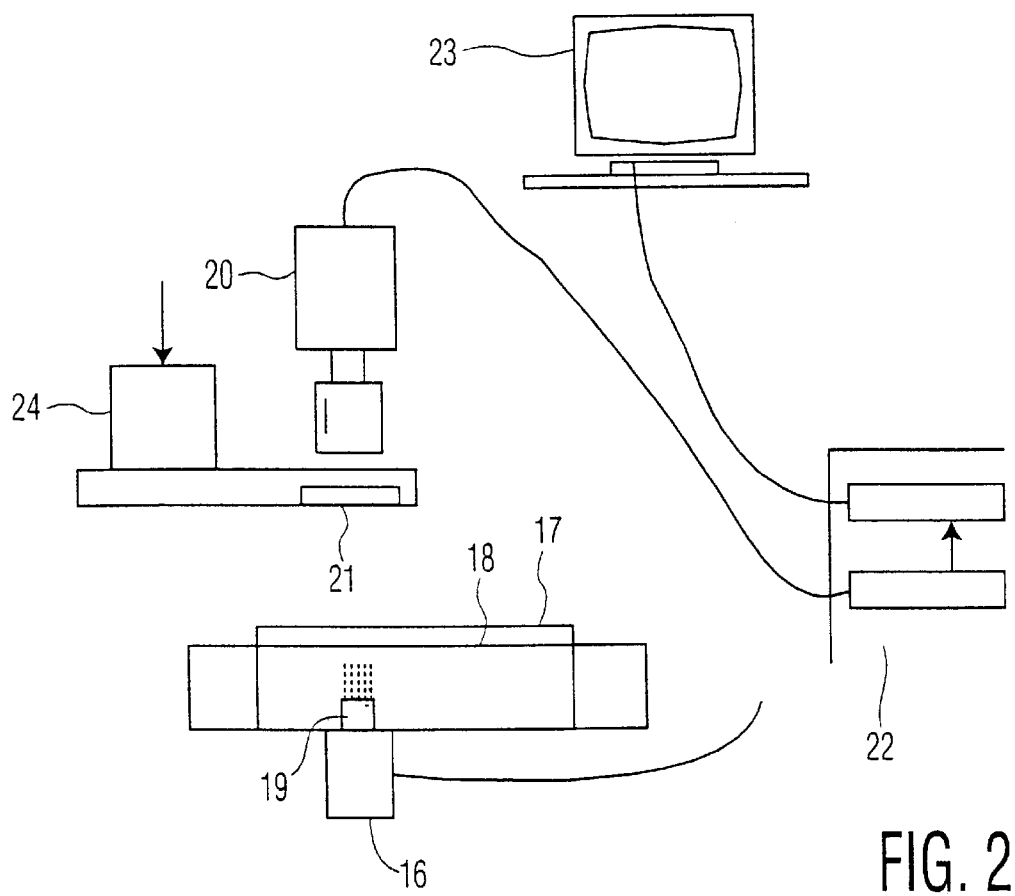
FIG. 2 is a schematic illustration of an embodiment of the method in accordance with the invention.

FIG. 2 illustrates the method and the device in accordance with the invention. Infrared radiation is emitted by an infrared source 16. A substrate 17 (in this example a display window of a cathode ray tube) is fixed in position. A phosphor layer 18 is applied to the display window. In this example, a collimator 19 is arranged between the infrared source and the substrate, so that the rays of infrared radiation incident on the substrate are substantially parallel to each other. The infrared radiation is at least partly passed by the substrate 17 and the phosphor layer 18. A camera 20 (in this example, a CCD camera) records the intensity of the passed infrared radiation. If, apart from infrared radiation, the source also emits other radiation (for example visible light), then a filter 21 passing infrared radiation may be arranged between the camera and the source. The measured value is fed into a computer 22. The results of these measurements can be visualized on a monitor 23. The CCD camera and the substrate can be moved relative to each other, so that the intensity can be measured in a number of places. The CCD camera 20 can be moved together with the filter by means of a stepping motor 24.

The intensity of the passed infrared radiation depends on the thickness of the phosphor layer, in a first-order approximation, in accordance with the formula:

$$T=T_0 e^{-s/t}$$

wherein T is the intensity of the passed infrared light, $T_0$ is the intensity of the radiation incident on the phosphor layer, s is a constant, and t is the thickness of the phosphor layer.

Consequently, if $T_0$ is known, the measurement of the intensity T yields the thickness of the phosphor layer. $T_0$ can be readily determined by a calibration measurement on a substrate without a phosphor layer. The constant s can be determined by a calibration measurement on a phosphor layer of known thickness. By measuring the transmission T at a number of points, the thickness distribution across a phosphor layer can be determined. The porosity can be determined as a result of the fact that, for holes in the phosphor layer, the intensity assumes a maximum value.

Figure 3:
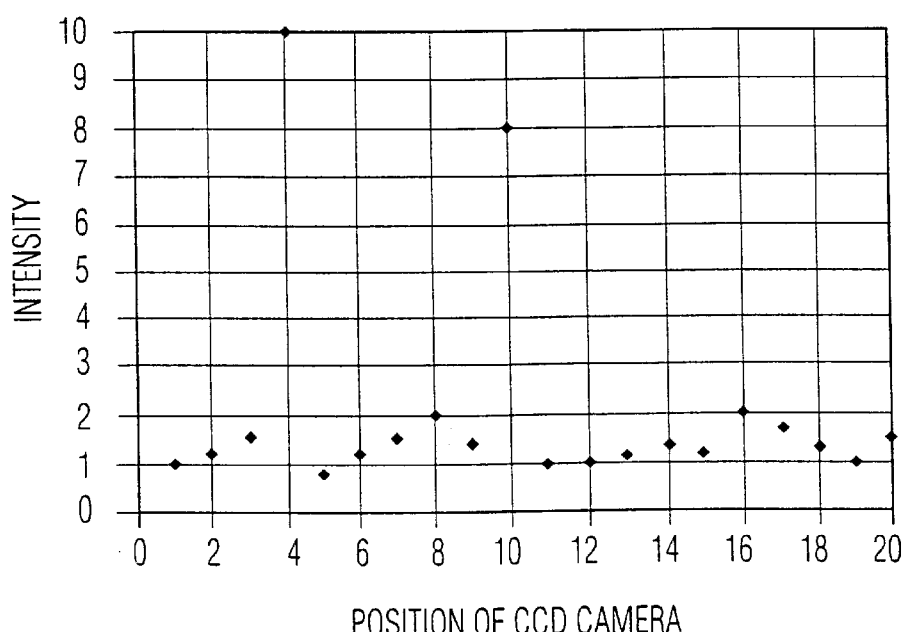
FIG. 3 illustrates transmission measurements on a number of points.

FIG. 3 schematically shows the intensity as a function of the position of the recording means (the CCD camera) along a line which corresponds to a phosphor line. The very high values for the measuring points 4 and 10 are caused by holes in the phosphor line (the maximum value corresponds to $I_0$); the variation in the other values is caused by a variation in the thickness of the phosphor line. Consequently, the measurement enables the average porosity to be determined (by means of the fraction of the measurements with an exceptionally high value, in this example 2 out of 20) as well as the average thickness of the layer (by determining and averaging the thicknesses of the other points) and the variation in thickness.

In the case of visible light and UV light it is not possible, or at least much more difficult, to determine the thickness of the phosphor layer from intensity measurements of transmitted light. In general, the absorption of the glass as well as the absorption of the phosphors is much greater, and these absorptions are also wavelength-dependent. Consequently, the intensity of the transmitted light is, at the same quantity of incident light, much smaller and, in addition, governed to a substantial decree by the exact composition and thickness of the substrate and the composition of the phosphors and the spectrum of the light source.

It will be obvious that within the scope of the invention many variations are possible. In the example, the invention is illustrated by means of a measurement on a phosphor layer on an inner surface of a display window of a cathode ray tube. The substrate may also form part of a lamp on which a phosphor layer is applied. Also properties of color filter layers (thickness, porosity) can be determined. The measurements can be used for selection purposes, that is timely identifying sub-standard phosphor screens or lamps and removing them from the production process. The measurements can also be used to influence the manufacture of phosphor screens.

The shape of phosphor dots (the position as well as the thickness and the thickness variation) can be determined.

A change in the manufacturing process will influence the shape, or the thickness, or the thickness variation. These changes can be measured in a simple and non-destructive manner by employing the method in accordance with the invention.

In FIG. 3, for example, the points 5 through 9 show the thickness variation of a phosphor layer across a phosphor dot. On the vertical axis measured transmission (on a relative scale of 1 to 10) is given, the horizontal axis denotes a number of measurements of points. On one side of a phosphor dot (point 5) the transmission is low, which corresponds to a relatively large thickness, while on the opposite side of the phosphor dot the transmission is relatively high, which corresponds to a relatively small thickness of the phosphor layer.

What is claimed is:

1. A method of determining a property of a of a mono-layer phosphor screen on a substrate, wherein the substrate and the layer are exposed to a beam of infrared radiation and, after passage through the mono-layer phosphor-screen and the substrate, a measurement of intensity of the beam is carried out.

2. A method as claimed in claim 1, wherein a substantially parallel beam of infrared radiation is sent through the substrate and the mono-layer phosphor screen.

3. A method as claimed in claim 1, wherein thickness of said mono-layer phosphor screen is determined from said measurement of intensity.

4. A method as claimed claim 1, wherein the substrate forms a display window of a cathode ray tube.

5. A method as claimed in claim 1, wherein the substrate is a part of a lamp.

6. A method as claimed in claim 1 wherein the porosity of said mono-layer phosphor screen is determined from said measurement of intensity.

7. A device for determining a property of a mono-layer phosphor screen on a substrate, wherein the device comprises a means for holding the substrate, and infrared source for emitting infrared radiation and a recording means for recording or measuring infrared radiation emitted by the source and passed by the substrate and the mono-layer phosphor screen.

8. A device as claimed in claim 7, wherein a means for collimating infrared radiation emitted by the source is situated between the source and the holding means.

* * * * *